United States Patent

Fischer

Patent Number: 5,286,875
Date of Patent: Feb. 15, 1994

[54] PREPARATION OF 5-HYDROXYETHYLPYRROLIDONES

[75] Inventor: Rolf Fischer, Heidelberg, Fed. Rep. of Germany

[73] Assignee: BASF Aktiengesellschaft, Ludwigshafen, Fed. Rep. of Germany

[21] Appl. No.: 960,776

[22] Filed: Oct. 14, 1992

[30] Foreign Application Priority Data

Oct. 17, 1991 [DE] Fed. Rep. of Germany ....... 4134303

[51] Int. Cl.$^5$ .......................................... C07D 207/26
[52] U.S. Cl. .................................................. 548/547
[58] Field of Search ....................................... 548/547

[56] References Cited

U.S. PATENT DOCUMENTS 4,874,865 10/1989 Wambach et al. ................ 546/243

FOREIGN PATENT DOCUMENTS 293740 5/1988 European Pat. Off. .

OTHER PUBLICATIONS

C. H. Hassall, Org. React., vol. 9, (1957) p. 73 et seq.
Journal of Organic Chemistry, vol. 51, Nr. 1, (1986) pp. 40–45.

Primary Examiner—David B. Springer
Attorney, Agent, or Firm—John H. Shurtleff

[57] ABSTRACT

A process for preparing a 5-hydroxyethylpyrrolidone of the general formula I

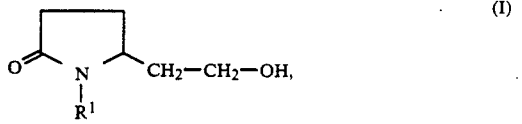

(I)

where $R^1$ is hydrogen, $C_1$- to $C_{12}$-alkyl, $C_3$- to $C_8$-cycloalkyl, aryl or $C_7$- to $C_{12}$-aralkyl, by reacting
a) a caprolactone of the general formula II

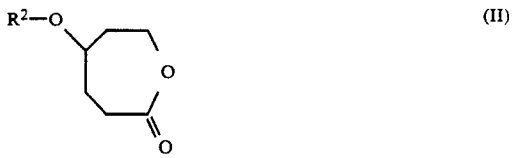

(II)

or
b) a butyrolactone of the general formula III

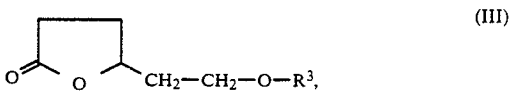

(III)

where
$R^2$ is $C_1$ to $C_{12}$-alkyl,

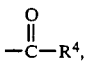

$R^3$ has the meaning of $R^2$ and is additionally hydrogen and
$R^4$ is $C_1$- to $C_8$-alkyl or phenyl,
with ammonia or a primary amine of the general formula IV $R^1$—$NH_2$ (IV)

where $R^1$ has the abovementioned meanings, at from 150° to 450° C. and at from 10 to 350 bar, and the preparation of the caprolactones II and the butyrolactones III from the cyclohexanones V.

3 Claims, No Drawings

PREPARATION OF 5-HYDROXYETHYLPYRROLIDONES

DESCRIPTION

The present invention relates to a process for preparing 5-hydroxyethylpyrrolidones from caprolactones or butyrolactones using ammonia or primary amines.

EP-A-293,740 discloses that 5-acetoxyethylpyrrolidone can be obtained by reacting pyrrolidone with vinyl acetate in the presence of di-tert-butyl peroxide.

C. H. Hassall, Org. React., Volume 9, (1957) page 73 et seq. additionally discloses the oxidation of ketones to give esters with the aid of peracids (Baeyer-Villiger oxidation). If cyclic ketones are employed, lactones are obtained, e.g. caprolactone from cyclohexanone.

J. Org. Chem. 51, pages 40 to 45 (1986) furthermore discloses that the 7-lactone of 4,6-dihydroxy-3,3,6-trimethylheptanoic acid is obtained by reacting 2,2,5,5-tetramethyl-4-hydroxycyclohexanone with m-chloroperbenzoic acid.

It is an object of the present invention to find a novel and convenient process for preparing 5-hydroxyethylpyrrolidones.

We have found that this object is achieved by a novel and improved process for preparing a 5-hydrodryethylpyrrolidone of the general formula I

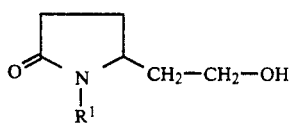
(I)

where $R^1$ is hydrogen, $C_1$- to $C_{12}$-alkyl, $C_3$- to $C_8$-cycloalkyl, aryl or $C_7$- to $C_{12}$-aralkyl, which comprises reacting a) a caprolactone of the general formula II

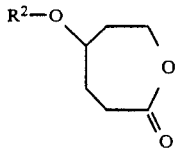
(II)

or b) a butyrolactone of the general formula III

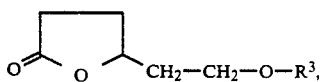
(III)

where
$R^2$ is $C_1$- to $C_{12}$-alkyl,

$R^3$ has the meaning of $R^2$ and is additionally hydrogen, and
$R^4$ is $C_1$- to $C_8$-alkyl or phenyl,
with ammonia or a primary amine of the general formula IV $$R^1-NH_2 \quad (IV)$$

where $R^1$ has the abovementioned meanings, at from 150° to 450° C. and 10 to 350 bar, and for preparing the caprolactones II and the butyrolactones III from the cyclohexanones V.

(V)

The process according to the invention for preparing 5-hydroxyethylpyrrolidones I can be carried out as follows:

The caprolactone II or the butyrolactone III can be reacted batchwise or, preferably, continuously with ammonia or a primary amine IV at elevated temperatures and elevated pressures in the gas phase, but particularly in the liquid phase.

The reaction can be carried out, for example, by heating a mixture of starting compound II or III and ammonia or primary amine in an autoclave, in the presence or absence of water or a solvent which is inert under the reaction conditions, under the self-adjusting autogenous pressure of the system until the reaction has taken place completely. The autoclave is then cooled and depressurized. The reaction products can be worked up in a manner known per se, for example by distillation or crystallization.

Ammonia and primary amines can be used in pure form or as aqueous ammonia and, if the amine is adequately water-soluble, as aqueous solutions.

Suitable primary amines are, e.g. alkylamines, cycloalkylamines, and furthermore arylamines and aralkylamines. Examples of primary amines of this type are methylamine, n-pentylamine, n-dodecylamine, cyclopentylamine, cyclohexylamine, aniline and benzylamine.

It is also possible to work in the presence of solvents which are inert under the reaction conditions. Solvents which can be used for this purpose are,, e.g. water, alcohols, ethers, hydrocarbons, aromatic compounds, chlorinated hydrocarbons or miscible mixtures thereof.

The reaction can be carried out at from 150° to 400° C., in particular 250° to 350° C. and at from 10 to 350 bar, preferably 50 to 250 bar. It is generally carried out in pressure vessels such as autoclaves under the autogenous pressure of the system. The reaction times are in general 0.5 to 5 hours. The molar ratio of ammonia or amine to caprolactone II or butyrolactone III is 0.5:1 to 50:1, in particular 1:1 to 20:1.

The caprolactones II can be prepared, e.g. by reacting cyclohexanones which are appropriately substituted in the 4-position with percarboxylic acids (Baeyer-Villiger oxidation).

The reaction can be carried out as follows: The cyclohexanone which is substituted in the 4-position by alkoxy or acyloxy groups is reacted in the liquid phase with a percarboxylic acid which is dissolved in a solvent which is inert under the reaction conditions.

The butyrolactones III can be prepared, e.g. by reacting 4-hydroxycyclohexanone with percarboxylic acids (Baeyer-Villiger oxidation).

4-hydroxycyclohexanone can be reacted with percarboxylic acids in the same manner as described for the 4-alkoxycyclohexanones and 4-acyloxycyclohexanones.

The reaction can be carried out, for example, by adding a solution of the peracid VI to the cyclohexanone V at the respective reaction temperature at the rate at which it reacts. Like the peracid VI, the cyclohexanone V can be added in a solvent. It is expedient, but not absolutely necessary, in this case to use the same solvent for the cyclohexanone V and the peracid VI. The course of the reaction can be monitored, e.g. by titration of the peracid used in each case. The reaction is generally continued until the cyclohexanone V has completely reacted. Traces of peracid/peroxide compounds can be destroyed, e.g. by subsequent heating or by addition of catalysts which catalyze the decomposition of peracid/peroxide compounds. The reaction mixtures can be worked up in a manner known per se, e.g. by distillation or crystallization.

Suitable peracids VI are all the customary peracids, e.g. performic acid, peracetic acid, perpropionic acid, trifluoroperacetic acid, monoperphthalic acid, perbenzoic acid, m-chloroperbenzoic acid and permaleic acid.

Suitable solvents are carboxylic acids, e.g. $C_1$- to $C_8$-carboxylic acids, preferably $C_1$- to $C_4$-carboxylic acids such as formic acid, acetic acid, propionic acid, chlorinated hydrocarbons such as methylene chloride, chloroform or 1,2-dichloroethane, or aromatic hydrocarbons such as benzene, toluene or xylenes. In general, the solvent should be stable under the reaction conditions.

Hydrogen peroxide, dissolved in a carboxylic acid, in the presence or absence of acidic catalysts, e.g. sulfuric acid or strongly acidic ion exchangers, can also be used. It is furthermore possible to react the cyclohexanones V with hydrogen peroxide in the presence of zeolite catalysts (U.S. Pat. No. 4,870,192).

The reaction can be carried out at from $-20°$ to $150°$ C., in particular $20°$ to $120°$ C. and at from 0.1 to 2 bar, preferably 0.5 to 1.3 bar, in general at atmospheric pressure (normal pressure).

The reaction can be carried out batchwise or continuously in the liquid phase.

The molar ratio of the peracid VI to the cyclohexanone V is 1:1 to 2:1, in particular 1:1 to 1.5:1.

The cyclohexanones V can be prepared, for example, by hydrogenating hydroquinone and hydroquinone derivatives in the presence of palladium catalysts.

The substituents $R^1$, $R^2$ and $R^3$ in the compounds I, II, III, IV, V and VI have the following meanings:

$R^1$ is hydrogen, $C_1$- to $C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, preferably $C_1$- to $C_8$-alkyl such as methyl, ethyl, n-propyl, isopropyl, n-butyl, isobutyl, sec-butyl, tert-butyl, n-pentyl, isopentyl, tert-amyl, n-hexyl, isohexyl, n-heptyl, isoheptyl, n-octyl and isooctyl, particularly preferably $C_1$- to $C_4$-alkyl such as methyl, ethyl, n-propyl, isopropyl, n-butyl, isobutyl, sec-butyl and tert-butyl, $C_3$- to $C_8$-cycloalkyl such as cyclopropyl, cyclobutyl, cyclopentyl, cyclohexyl, cycloheptyl and cyclooctyl, preferably cyclopentyl, cyclohexyl and cyclooctyl, $C_7$- to $C_{12}$-aralkyl, preferably $C_7$- to $C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $R^2$ and $R^3$ are $C_1$- to $C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, preferably $C_1$- to $C_.$-alkyl such as methyl, ethyl, n-propyl, isopropyl, n-butyl, isobutyl, sec-butyl, tert-butyl, n-pentyl, isopentyl, tert-amyl, n-hexyl, isohexyl, n-heptyl, isoheptyl, n-octyl and isooctyl, particularly preferably $C_1$- to $C_4$-alkyl such as methyl, ethyl, n-propyl, isopropyl, n-butyl, isobutyl, sec-butyl and tert-butyl; or

$$-\overset{\overset{\displaystyle O}{\|}}{C}-R^4$$

$R^3$ is additionally hydrogen, and $R^4$ is $C_1$- to $C_8$-alkyl such as methyl, ethyl, n-propyl, isopropyl, n-butyl, isobutyl, sec-butyl, tert-butyl, n-pentyl, isopentyl, tert-amyl, n-hexyl, isohexyl, n-heptyl, isoheptyl, n-octyl and isooctyl, preferably $C_1$- to $C_4$-alkyl such as methyl, ethyl, n-propyl, isopropyl, n-butyl, isobutyl, sec-butyl and tertbutyl, particularly preferably methyl and ethyl, or phenyl.

The 5-hydroxyethylpyrrolidones I, the caprolactones II, the 5-ethylenebutyrolactones III and the cyclohexanones V which can be prepared by the process according to the invention are important intermediates for the synthesis of drug precursors such as, e.g. 5-vinylpyrrolidone (U.S. Pat. No. 4,235,778, U.S. Pat. No. 3,959,356).

5-Vinylpyrrolidone, which is an intermediate for the synthesis of the antiepileptic vinyl-GABA, is obtained by elimination of water, or by elimination of acetic acid after acetylation.

EXAMPLES

Example 1

Preparation of 5-hydroxyethylbutyrolactone

A solution of 80 g of m-chloroperbenzoic acid in 500 ml of chloroform was added dropwise at 40° C. to a solution of 34.3 g of 4-hydroxycyclohexanone in 100 ml of chloroform in the course of 45 minutes. The reaction mixture was stirred at 40° C. for 2 hours. The precipitated m-chlorobenzoic acid was filtered off with suction. The filtrate was exhaustively extracted with water. The combined aqueous extracts were peroxide-free. They were concentrated on a rotary evaporator (50° C./20 mbar) and then subjected to a short path distillation. 33.9 g of 5-hydroxyethylbutyrolactone (86%, based on the 4-hydroxycyclohexanone employed) of boiling point 124°-130° C./0.2 mbar were obtained.

Example 2

Preparation of mixtures of 5-hydroxyethylbutyrolactone and 5-acetoxyethylbutyrolactone A solution of 11.4 g of 4-hydroxycyclohexanone in 30 g of glacial acetic acid was treated at 80° C., with stirring, in the course of 10 minutes with 80.9 g of equilibrium peracetic acid (14.1% by weight of peracetic acid, prepared by stirring 34 g of 50% strength $H_2O_2$ with 215 g of glacial acetic acid in the presence of 10 g of strongly acidic ion exchanger (Amberlite IR 120, H-form). After stirring at 20° C. for 16 hours, the ion exchanger was filtered off. The reaction mixture was stirred at 80° C. for 3.5 hours. It was then found by titration that only traces of percompounds were still present. After concentration of the reaction mixture (50° C./30 mbar), a short path distillation was carried out. In this case, 12.5 g of a product mixture (boiling point 105°-115° C./0.2 mbar) were obtained, which according to gas-chromatographic analysis consisted to 91% of 5-acetoxyethylbutyrolactone (yield 66%) and to 9% of 5-hydroxyethylbutyrolactone (yield 9%). Both yield data relate to the 4-hydroxycyclohexanone employed.

Example 3

Preparation of 5-hydroxyethylpyrrolidone 22.1 g of 5-hydroxyethylbutyrolactone was stirred with 120 g of 25% strength aqueous ammonia for one hour at 330° C./210 bar in an autoclave. The reaction product was concentrated (50° C./30 mbar) and subjected to a short path distillation. In this way, 13.8 g of 5-hydroxyethylpyrrolidone (63%) (boiling point 150°-170° C./0.2 mbar; melting point 52°-52.5° C. from acetone/methyl tert-butyl ether) were obtained.

Example 4

Preparation of 4-acetoxycaprolactone 50 g of 4-acetoxycyclohexanone, dissolved in 150 ml of chloroform, were treated at 40° C. in the course of 40 minutes, with stirring, with 136 g of m-chloroperbenzoic acid (55% strength), dissolved in 500 ml of chloroform. The reaction mixture was stirred at 40° C. for 2 hours. After cooling to room temperature, the precipitated solid (m-chlorobenzoic acid), was filtered off with suction. The chloroform phase was extracted twice by shaking with 20% strength aqueous sodium carbonate solution, dried over sodium sulfate and concentrated on a rotary evaporator. 46.4 g of 4-acetoxycaprolactone (84%, based on the 4-acetoxycyclohexanone employed) were recovered from the residue obtained in this way by bulb tube distillation.

$^{13}C$-NMR spectrum ($CDCl_3$) δ[ppm]=21.1 ($CH_3$), 27.5 ($CH_2$), 28.4 ($CH_2$), 33.9 ($CH_2$), 63.5 ($CH_2$), 70.0 (CH), 169.9 (C=O), 175.0 (C=O).

$^1H$-NMR spectrum ($CDCl_3$) δ[ppm]=2.0 (2H,m), 2.1 (2H,m), 2.1 (3H,S), 2.5 (1H,m), 2.9 (1H,M), 4.2 (1H,m), 4.45 (1H,m, 5.1 (1H,m).

Example 5

Preparation of 5-hydroxyethylpyrrolidone 22.4 g of 4-acetoxycaprolactone were stirred for 1 hour at 330° C. in an autoclave together with 100 g of 25% strength aqueous ammonia. After cooling and depressurizing the autoclave, the reaction product was concentrated on a rotary evaporator (40° C./30 mbar) and purified by short path distillation. In this case, 10.1 g of 5-hydroxyethylpyrrolidone were obtained (61%, based on the 4-acetoxycaprolactone employed) and identified by NMR spectroscopy.

Example 6

Preparation of 4-methoxycaprolactone 14.8 g of 4-methoxycyclohexanone were reacted with m-chloroperbenzoic acid and the mixture was worked up in the same manner as described in Example 4. In this way, 9 g of 4-methoxycaprolactone ($n_d^{20}$=1.4737) (54%, based on the 4-methoxycyclohexanone employed) were obtained.

$^{13}C$-NMR spectrum ($CDCl_3$) δ[ppm]=26.9 ($CH_2$), 27.8 ($CH_2$), 33.6 ($CH_2$), 55.9 ($CH_3$), 63.4 ($CH_2$), 75.6 (CH), 176.1 (C=O).

$^1H$-NMR spectrum ($CDCl_3$) δ[ppm]=1.85 (1H,m), 2.0 (3H,m), 2.4 (1H,q), 2.95 (1H,t), 3.35 (3H,s), 3.6 (1H,m), 4.1 (1H,q), 4.5 (1H,t).

Example 7

Preparation of 5-hydroxyethylpyrrolidone 30 g of 4-methoxycaprolactone were stirred at 330° C. for 1 hour together with 100 g of 25% strength aqueous ammonia in the same manner as described in Example 4. After cooling and depressurizing the autoclave and working up the reaction mixture by distillation, 9.1 g of 5-hydroxyethylpyrrolidone were obtained (34%, based on the 4-methoxycaprolactone employed) and identified by NMR spectroscopy.

We claim:

1. A process for preparing a 5-hydroxyethylpyrrolidone of the general formula I

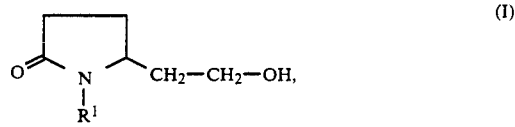

where

R$^1$ is hydrogen, C$_1$- to C$_{12}$-alkyl, C$_3$- to C$_8$-cycloalkyl, aryl or C$_7$- to C$_{12}$-aralkyl, which comprises reacting a) a caprolactone of the general formula II

or b) a butyrolactone of the general formula III

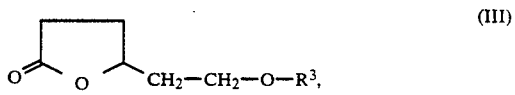

where

R$^2$ is C$_1$- to C$_{12}$-alkyl or

R³ has the meaning of R² and is additionally hydrogen, and

R⁴ is $C_1$- to $C_8$-alkyl or phenyl, with ammonia or a primary amine of the general formula IV $$R^1-NH_2 \quad (IV)$$

where R¹ has the abovementioned meanings, at from 150° to 450° C. and 10 to 350 bar.

2. The process for preparing a 5-hydroxyethylpyrrolidone of the general formula I as claimed in reaction a) of claim 1, wherein the caprolactone of the general formula II is obtained by reacting a cyclohexanone of the general formula V

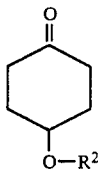

(V)

in which R² has the abovementioned meanings, with a peracid of the general formula VI

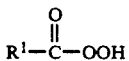

(VI)

in which R¹ has the abovementioned meanings, at from −20° to +150° C. and at from 0.1 to 2 bar.

3. The process for preparing a 5-hydroxyethylpyrrolidone of the general formula I as claimed in reaction b) of claim 1, wherein a butyrolactone of the general formula III is obtained by reacting a 4-hydroxycyclohexanone of the general formula VII

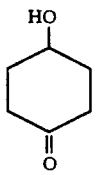

(VII)

with a peracid of the general formula VI

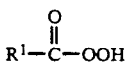

(VI)

where R¹ has the abovementioned meanings, at from −20° to +150° C. and at from 0.1 to 2 bar.

* * * * *